United States Patent [19]

Kozlow

[11] Patent Number: 4,586,691
[45] Date of Patent: May 6, 1986

[54] SAFETY SLIDE CLAMP

[75] Inventor: Gary W. Kozlow, Encinitas, Calif.

[73] Assignee: Warner-Lambert Company, Morris Plains, N.J.

[21] Appl. No.: 733,667

[22] Filed: May 13, 1985

[51] Int. Cl.[4] ............................................. F16L 55/14
[52] U.S. Cl. ....................................... 251/7; 604/250
[58] Field of Search ................... 251/4, 7, 8; 604/250

[56] References Cited

U.S. PATENT DOCUMENTS

| | | | |
|---|---|---|---|
| 2,715,905 | 8/1955 | Ogle | 128/214 |
| 2,775,240 | 12/1956 | Morrisey, Jr. et al. | 128/214 |
| 2,889,848 | 6/1959 | Redmer | 251/7 |
| 3,216,418 | 11/1965 | Scislowicz | 128/214 |
| 3,316,935 | 5/1967 | Kaiser et al. | 137/595 |
| 4,142,524 | 3/1979 | Jassawalla et al. | 128/214 F |
| 4,155,362 | 5/1979 | Jess | 128/214 F |
| 4,187,057 | 2/1980 | Xanthopoulos | 417/63 |
| 4,230,151 | 10/1980 | Jonsson | 251/7 |
| 4,411,652 | 10/1983 | Kramer et al. | 604/153 |
| 4,439,179 | 3/1984 | Lueders et al. | 251/7 |
| 4,524,802 | 6/1985 | Lawrence et al. | 251/7 |

Primary Examiner—Martin P. Schwadron
Assistant Examiner—Sheri M. Novack
Attorney, Agent, or Firm—Neil K. Nydegger

[57] ABSTRACT

A safety slide clamp to prevent free flow when tubing is disconnected from an I.V. administration device comprises a blade formed with a tear-drop shaped aperture through which the tubing is positioned. The aperture includes an enlarged portion and a narrow portion which is tapered to form a slot that is engageable with the tubing to prevent flow therethrough. A base formed with a well is attached to the pump and is adapted to slidably receive the blade of the slide clamp. Retaining means formed on the base are spaced to support the blade and retain the tubing in a recess between the fingers and the base. Placement of the tubing into the recess and subsequent insertion of the blade into the well permits operational fluid flow through the tube. Subsequent retraction of the blade urges the tubing into the slot to prevent free flow from the tube upon its removal from the device.

3 Claims, 6 Drawing Figures

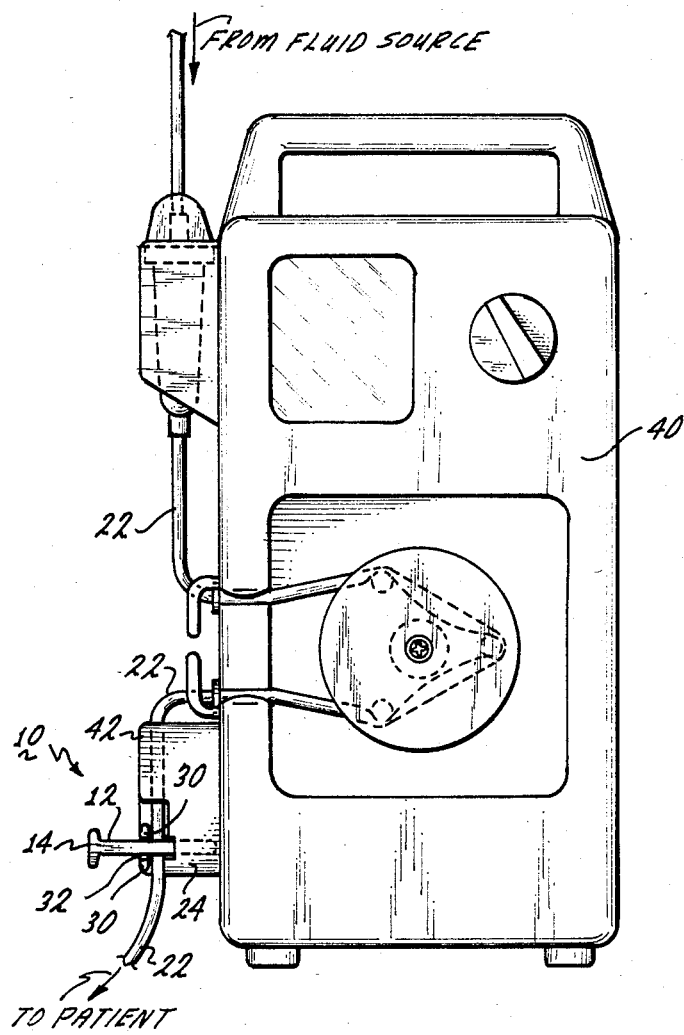
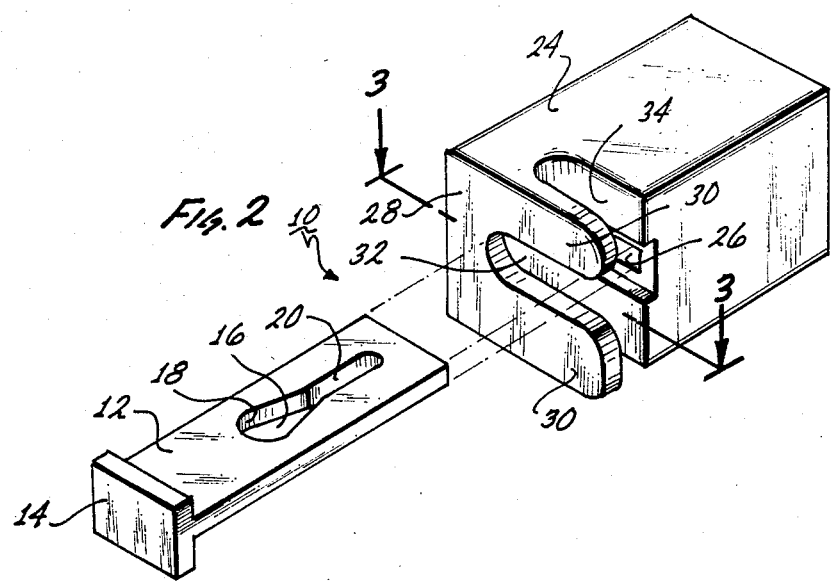
Fig. 1
Fig. 2

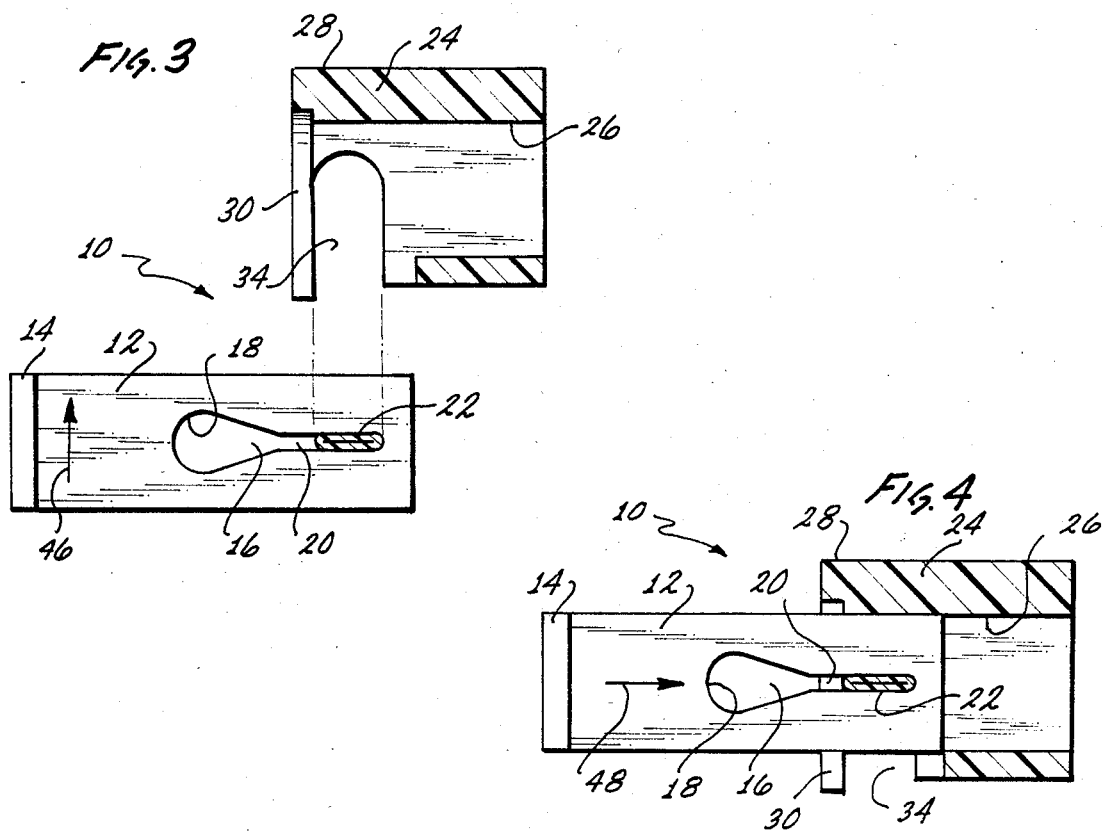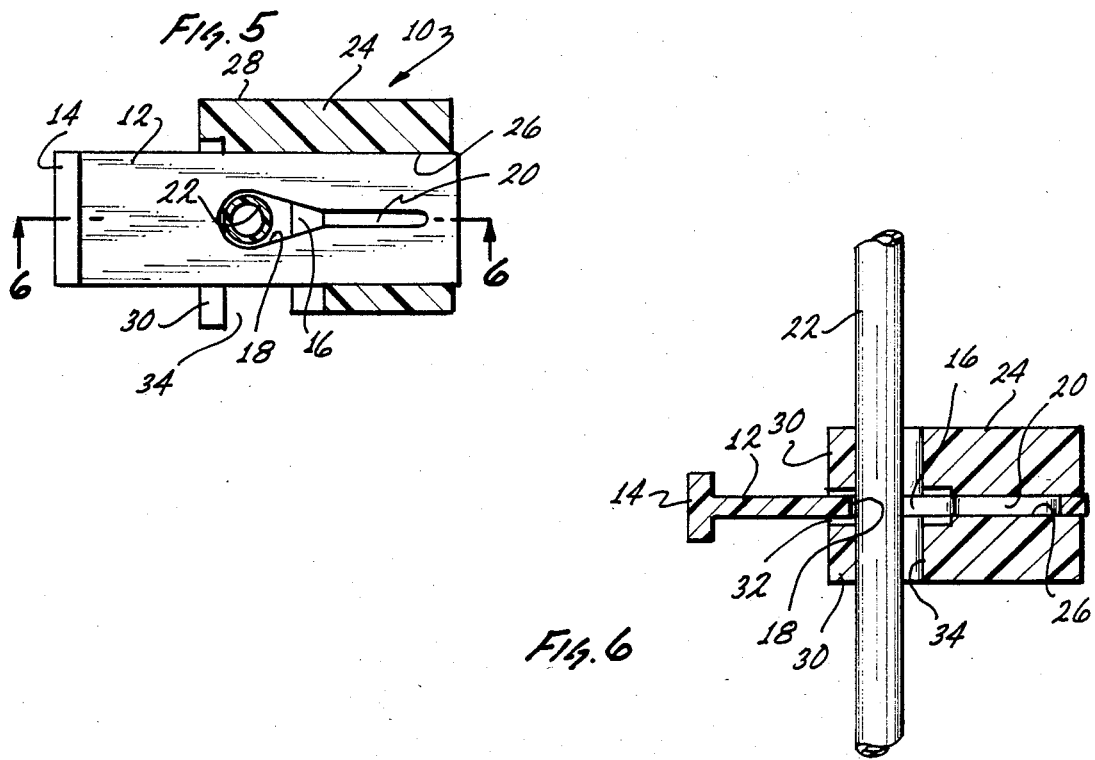

SAFETY SLIDE CLAMP

BACKGROUND OF THE INVENTION

This invention relates generally to clamping devices used with resilient tubing. Specifically, this invention pertains to a slide clamp which is usable with an I.V. administration system to prevent unwanted free flow of fluid through the I.V. tubing. More specifically, this invention pertains to a clamping device which insures that the I.V. tubing is constricted upon being disengaged or disconnected from an I.V. administration system. This invention is particularly, but not exclusively, useful as a safety slide clamp for the prevention of free flow through a resilient I.V. tube when such a tube is used with a rotary peristaltic pump for the administration of I.V. fluids to a patient.

DESCRIPTION OF THE PRIOR ART

The use of clamping devices to occlude or constrict I.V. tubing and prevent unwanted fluid flow therethrough is well known in the art. For example, independent hand-operated slide clamps, roller clamps and pinch clamps are commonly used throughout the medical profession to control fluid flow through I.V. tubes. However, in I.V. systems which incorporate a fluid flow device, such as a pump or a controller, there is often a need for a more sophisticated clamping device. More specifically, it may even be desirable to have a clamp which is operatively associated with the fluid flow device. In such systems an independently operated clamp can create unwanted problems.

In specific instances where I.V. solutions are being parenterally administered to a patient, it is important that I.V. tube clamps be incorporated into the I.V. administration system which will prevent the unwanted free flow of fluids to the patient. The problem can be particularly aggravating when the system includes a peristaltic type pump which requires a normally patent fluid line for its operation. With such a pump, some means is needed to automatically insure that unwanted fluid free flow does not occur when the tubing of the fluid line is disengaged from the pump.

Although the present invention is adaptable for use with a peristaltic pump, it will be appreciated by the skilled artisan that the device of the present invention can be incorporated into any type of an I.V. administration system. More specifically, the present invention could easily be used with an I.V. pump type system such as the one disclosed in U.S. Pat. No. 3,985,133 to Jenkins and assigned to the assignee of the present invention. Also, it will be appreciated by the skilled artisan that the present invention can be used with controllers such as the system disclosed in U.S. Pat. No. 4,300,552 to Cannon and assigned to the assignee of the present invention.

Accordingly, it is an object of the present invention to provide a safety slide clamp which must be activated to constrict the I.V. tube in order to disengage the I.V. tube from an I.V. administration device. It follows that another object of the present invention is to provide a simple to use clamp which insures that the I.V. tube cannot be disconnected or disengaged from the I.V. infusion device when the tube is patent. Still another object of the present invention is to provide a cost effective, easy to manufacture and simple to use safety slide clamp for engagement with the I.V. tube of an I.V. infusion device.

SUMMARY OF THE INVENTION

The preferred embodiment of the novel safety slide clamp for use with an I.V. infusion device comprises a base member which is formed with a well. A bracket having a pair of substantially parallel retaining fingers which form a slit between the fingers is disposed on the base member to establish a U-shaped recess between the retaining fingers and the area of the base near the opening to the well. The bracket may either be mounted on the base by a means well known in the pertinent art or may be formed integral with the base. The safety slide clamp of the present invention further comprises a slide clamp having a blade formed with a tear drop shaped aperture for receiving the I.V. tube therethrough. The blade, when urged against the I.V. tube to constrict the tube within the narrow part of the aperture, is engageable with the base to place the I.V. tube in the recess and position the blade in the slit between the retaining fingers for slidable insertion into the well. Upon insertion of the blade into the well, the I.V. tube is repositioned into the broader part of the aperture of the blade to permit fluid flow therethrough. With the blade in the well, the I.V. tube is retained in the recess by structural constraints created by the cooperation of the base, the retaining fingers and the blade.

Removal of the I.V. tube from the base is accomplished by retracting the blade from the well. This causes reengagement of the I.V. tube with the narrow portion of the blade's aperture to constrict the I.V. tube and prevent fluid flow therethrough. In this configuration, the constricted I.V. tube and the associated blade can be disengaged from the base.

The novel features of this invention, as well as the invention itself, both as to its organization and operation will be best understood from the accompanying drawings taken in conjunction with the accompanying description in which similar reference characters refer to similar parts and in which:

BRIEF DESCRIPTION OF THE DRAWINGS

FIG. 1 is a front view of an I.V. infusion device in association with the present invention;

FIG. 2 is an exploded perspective view of the present invention;

FIG. 3 is an exploded cross-sectional view of the safety slide clamp as seen along the line 3—3 in FIG. 2 with the blade constricting an I.V. tube and positioned for engagement with the base;

FIG. 4 is a top cross-sectional view of the present invention as seen in FIG. 3 with the blade constricting an I.V. tube and positioned on the base of the present invention;

FIG. 5 is a top cross-sectional view of the present invention as seen in FIG. 4 with the blade inserted into the base to provide for a patent I.V. tube; and FIG. 6 is a side cross-sectional view of the present invention as seen along the line 6—6 in FIG. 5.

DESCRIPTION OF THE PREFERRED EMBODIMENT

The environment of the present invention is as seen in FIG. 1 wherein the safety slide clamp, generally designated 10, is shown in its association with a peristaltic pump 40. Referring now to FIG. 2 for greater detail of the present invention, it can be seen that the present invention includes a blade 12 which has a handle 14. Formed into blade 12 is a tear drop shaped aperture 16 having an enlarged portion 18 and a narrow portion defining a slot 20. As will be appreciated by a person of ordinary skill, blade 12 can be formed with any of several configurations for the aperture 16. Such a configuration could include tapered regions connecting the enlarged portion 18 with the slot 20. Preferably, aperture 16 is oriented on blade 12 so that its longitudinal axis coincides with the longitudinal axis of blade 12.

Also shown in FIG. 2 is a base 24 which is formed with a well 26 having sufficient depth and cross-sectional area to operatively receive blade 12 for purposes to be subsequently discussed. A bracket 28 is either mounted on base 24 by any means well known in the art or, as is shown in the embodiment in FIG. 2, bracket 28 is integrally formed with the base 24. A pair of retaining fingers 30 constitute a portion of bracket 28 and are mounted substantially parallel thereon to form a slit 32. Slit 32 is aligned with well 26 in a manner that permits the holding of a portion of blade 12 within slit 32 while blade 12 is inserted into well 26. As is best seen with reference to FIGS. 2-5, retaining fingers 30 of bracket 28, together with the base 24, form a U-shaped recess 34 which is of sufficient width to receive an I.V. tube 22 therein. As best seen in FIG. 2, the longitudinal axis of recess 34 is substantially perpendicular to the longitudinal axis of well 26. Accordingly, when I.V. tube 22 is placed into recess 34, the axis of I.V. tube 22 will be substantially perpendicular to blade 12.

As will be appreciated by a person of ordinary skill in the pertinent art, the safety slide clamp 10 of the present invention can be associated with various other devices to help provide for the safe operation of an I.V. infusion system. For example, as shown in FIG. 1, the safety slide clamp 10 of the present invention is incorporated with an air-in-line detector 42 and mounted on the side of peristaltic pump 40.

OPERATION

Referring now to FIG. 3, it can be seen that prior to engagement with base 24, blade 12 of the safety slide clamp 10 is manipulated by the operator to place I.V. tube 22 into slot 20 of blade 12 to thereby constrict I.V. tube 22. Blade 12 is engaged with base 24 by moving blade 12 in the direction indicated by the arrow 46 in FIG. 3. After this movement, blade 12 is positioned with respect to the base 24 substantially as shown in FIG. 4. As seen in FIG. 4, I.V. tube 22 is positioned within the recess 34 and blade 12 is positioned within slit 32 between the retaining fingers 30. Further engagement of the blade 12 with base 24 is accomplished by urging against handle 14 of blade 12 in the direction indicated by arrow 48 in FIG. 4. This action inserts blade 12 into well 26. The insertion of blade 12 into well 26 of base 24 also causes base 24 to urge against I.V. tube 22 and relocate I.V. tube 22 within aperture 16 from slot 20 into enlarged portion 18.

As best seen with reference to FIG. 5, when blade 12 is inserted into well 26 of base 24, I.V. tube 22 is patent and permits the flow of fluid therethrough. This cooperation of structure is also shown in FIG. 6 wherein I.V. tube 22 is shown in its position within recess 34 and in enlarged portion 18 of aperture 16. Also, it should be appreciated that with blade 12 engaged with base 24 in the manner shown in FIGS. 1, 5 and 6, I.V. tube 22 cannot be disengaged from pump 40 by an action on I.V. tube 22. For example, an attempt to remove I.V. tube 22 from recess 34 by pulling on I.V. tube 22 in a direction opposite to arrow 46 will be prevented by the action of base 24 on blade 12 since blade 12 is inserted into well 26. Further, an attempt to remove blade 12 from well 26 by pulling on I.V. tube 22 in a direction opposite to arrow 48 will be prevented by the action of fingers 30 against I.V. tube 22.

Proper disengagement of I.V. tube 22 from infusion device 40 is accomplished by taking steps in the reverse order required for engaging I.V. tube 22 with safety slide clamp 10. Therefore, consider sequentially FIGS. 5, 4 and 3. Withdrawal of the blade 12 is accomplished by grasping handle 14 and pulling blade 12 in a direction opposite to the indication shown for arrow 48. This motion causes tapered slot 20 of aperture 16 to engage with I.V. tube 22 and constrict I.V. tube 22. It can now be seen by cross-reference between FIG. 4 and FIG. 3 that I.V. tube 22 when constricted in tapered slot 20 of blade 12 can be moved in a direction opposite to the indication of arrow 46 to remove the constricted I.V. tube 22 from recess 34. Accordingly, it will be appreciated by the skilled artisan that I.V. tube 22 cannot be disengaged from the safety slide clamp 10 when I.V. tube 22 is patent.

While the particular safety slide clamp as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the apended claims.

I claim:

1. A safety clamp for use with an I.V. administration device to prevent unwanted free flow through an I.V. tube which comprises:

a blade formed with an aperture for receiving the tube therein, said aperture having an enlarged portion and a tube constricting slot extending therefrom, said blade slidably engagable with the tube for movement between a first position wherein said tube is located in said slot and a second position wherein said tube is located in said enlarged portion;

a base mounted on the device and formed with a well having an opening;

a retaining means comprising a bracket having a pair of substantially parallel fingers extending therefrom to form a slit between said fingers, said retaining means positioned on said base to place said bracket adjacent said opening and superpose said fingers above said opening to form a U-shaped recess between said fingers, said bracket and said base, said recess for receiving the tube therein only when said blade is in said first position and for moving said blade through said slit to locate said blade for insertion into said well and simultaneous movement of said blade into said second position.

2. a safety slide clamp as recited in claim 1 wherein the longitudinal axis of said recess is substantially perpendicular to the longitudinal axis of said well.

3. A safety slide clamp as recited in claim 2 wherein said enlarged portion of said aperture gradually tapers into said slot for constricting the tube.

* * * * *